United States Patent [19]

Ashman et al.

[11] Patent Number: 5,246,442
[45] Date of Patent: Sep. 21, 1993

[54] SPINAL HOOK

[75] Inventors: Richard B. Ashman, Dallas, Tex.; Michael C. Sherman, Memphis, Tenn.

[73] Assignee: Danek Medical, Inc., Memphis, Tenn.

[21] Appl. No.: 815,492

[22] Filed: Dec. 31, 1991

[51] Int. Cl.$^5$ ............................................... A61F 5/00
[52] U.S. Cl. ............................................. 606/61; 606/72
[58] Field of Search .................... 606/60, 61, 62, 64, 606/72, 73

[56] References Cited

U.S. PATENT DOCUMENTS

| | | | |
|---|---|---|---|
| 4,567,884 | 2/1986 | Edwards | 606/61 |
| 4,648,388 | 3/1987 | Steffee | 606/61 |
| 4,815,453 | 3/1989 | Cotrel | 606/61 |
| 5,002,542 | 3/1991 | Frigg | 606/61 |
| 5,007,909 | 4/1991 | Rogozinski | 606/61 |

OTHER PUBLICATIONS

TSRH Surgical Technique Manual of Danek Medical, Inc. (1990).

Primary Examiner—Richard J. Apley
Assistant Examiner—Linda C. M. Dvorak

[57] ABSTRACT

A new spinal hook of the present invention which comprises a hook-configured shoe with an integral portion. The top portion includes a pair of central posts which are displaced to form a slot therebetween. Each central post includes a groove colinearly formed to receive a spinal rod within. The slot between the two posts is oriented with respect to the grooves so that an eyebolt assembly may be used to engage the hook to the fixation rod. In another aspect of the invention, a slot is formed in the end faces of the hook. The slot forms one part of a tongue and slot instrumentation engagement arrangement, with the hook-holding instrument including a correspondingly configured tongue. In another aspect of the invention, each of the pair of central posts include grooves on both lateral faces of the posts so that the spinal rod can be situated on either side of the spinal hook.

7 Claims, 2 Drawing Sheets

SPINAL HOOK

BACKGROUND OF THE INVENTION

The present invention concerns spinal fixation systems, and particularly spinal hooks for engaging portions of a vertebra. More specifically, the present invention concerns improvements in the manner of connecting the spinal hook to a rod used in the spinal fixation system.

Several techniques and systems have been developed for correcting and stabilizing spinal curves and facilitating spinal fusion. In one system, a bendable rod is longitudinally disposed adjacent the vertebral column and is fixed to various vertebra along the length of the column by way of a number of fixation elements. A variety of fixation elements can be provided which are configured to engage specific portions of the vertebra.

The present invention specifically concerns one type of fixation element, that is a spinal compression/distraction hook of the type used in connection with the bendable rod. The spinal hooks are used to anchor the rod relative to the spinal column, as well as to provide a path for compression or distraction loading of the vertebra.

An example of one such system is the TSRH ™ spinal system of Danek Medical, Inc. In this system, a spinal hook, such as hook H shown in FIG. 1, is engaged to the fixation rod R by way of an eyebolt assembly E. As is known in the art, the eyebolt E is threaded onto the spinal rod and captured within yokes on the spinal hook. A nut is threaded onto the threaded post of the eyebolt to clamp the yoke between the nut and the fixation rod R. The eyebolt E and hook yokes provide three degrees of fixation as represented by the arrows in FIG. 1. Details of the TSRH ™ spinal implant system are disclosed in the "TSRH ™ Surgical Technique Manual" provided by Danek Medical, Inc. published in 1990 which disclosure is incorporated herein by reference.

It is the goal of the surgeon using such spinal implant systems as the Danek TSRH ™ system to apply the vertebral fixation elements, such as the spinal hook, to the spine in the appropriate anatomic position, and then to engage each fixation element to the spinal rod. It has been found that in spite of the great benefits provided by the double-yoke spinal hooks, such as hook H in FIG. 1, certain problems arise which have heretofore not been adequately addressed.

One problem with the spinal hooks H of the prior art is that the hooks are rather bulky and wide since the fixation yokes of the hook are configured to surround the spinal rod R. The size or bulkiness of the spinal hook is an especially important problem since a significant portion of the patient population for spinal implant systems of this type (namely the TSRH ™ system) is made up of pediatric patients. Bulky implants are not easily implanted into small, thin people because the space around the vertebra is not great.

In patients with severe deformities of the spinal column, the rod must be contoured to meet the deformity. Prior art hooks, such as hook H, only allow the rod to be implanted in one position relative to the spinal column as dictated by the required position of the blade of the spinal hook. There is therefore a need for a spinal hook that can be fixed in more than one position on the rod, thereby allowing the rod to be implanted in more than one position relative to the spinal column.

Another problem with the spinal hooks H of the prior art is that the instrumentation used to engage the hook and hold it for insertion is often difficult to engage to the hook and can be susceptible to a fragile engagement between the instrumentation and the hook. For example, in one prior art embodiment of the spinal hook H, pin holes P are situated in each of the four posts of the double-yoke hook. The pin holes P are designed so that they receive the pins of a hook holder. Such hook-holding instruments incorporate four or eight pins to correspond to the number of pinholes in the hook (which in the case of the hook H in FIG. 1 is 8 pinholes). Engagement of the pins to the pinholes is often difficult as all the components must be aligned perfectly for the instrument to be locked into place. Moreover, as the hook-holding instrument is manipulated to properly position the spinal hook about a lamina L (as shown in FIG. 2), there is a risk that the pins will become disengaged with the pinholes P. It has been found that these frailties of the present hooks H as shown in FIGS. 1 and 2 can often lead to significant amounts of manipulation in order to properly implant the hook.

As shown in FIG. 2, the placement of the spinal hook H and engagement of the hook to the rod R by way of the eyebolt assembly E must frequently occur in very tight quarters. In one particular application shown in FIG. 2, the hook is oriented between the L2 and L3 lumbar vertebra so that the hook engages the lamina L of the L2 vertebra. It can certainly be appreciated that in smaller patients, such as pediatric patients, the room to manipulate the spinal hook to engage it to the rod is very limited.

There is therefore a need for a new spinal hook configuration which is less bulky and easier to engage than the spinal hooks previously known. There is also a need for such a spinal hook which can be more easily engaged to the spinal rod, preferably on either side of the rod as required by the spinal anatomy.

A new spinal hook is offered by the present invention which has a smaller profile and which includes means for more easily engaging a hook holder instrument for implanting the hook. More particularly, and in one aspect of the invention, the spinal hook comprises a hook-configured shoe to which a central post top is engaged. The top portion includes a pair of central posts which are displaced to form a slot therebetween. Each central post includes a groove colinearly formed to receive a spinal rod within. The slot between the two posts is oriented with respect to the grooves so that an eyebolt assembly may be used to engage the hook to the fixation rod.

In another aspect of the invention, a slot is formed in the end faces of the hook. The slot forms one part of a tongue and slot instrument engagement arrangement, with the hook-holding instrument including a correspondingly configured tongue. The tongue of the hook-holder instrument engages within the slot on each central post of the hook to provide a more substantial engagement as the hook is being implanted.

In another aspect of the invention, each of the pair of central posts include grooves on both lateral faces of the posts so that the spinal rod can be situated on either side of the spinal hook. Thus, the spinal hook of the present invention is more readily adaptable to various spinal anatomies without requiring that the spinal rod be bent in the saggital plane in order to contact the spinal hook.

It is one object of the spinal hook of the present invention to reduce the overall profile of the spinal fixation system, and particularly the components used to engage the vertebra of the patient.

It is another object to provide such a hook which incorporates a tongue and slot arrangement for a firm, solid and easy engagement to a hook-holding instrument.

Related objects and advantages of the present invention will be apparent from the following description.

DESCRIPTION OF THE PREFERRED EMBODIMENTS

Figure 3:
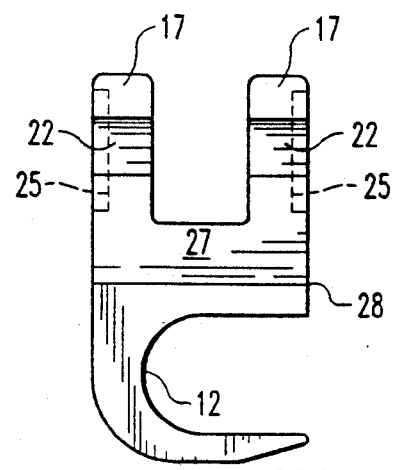
FIG. 3 is a side elevational view of a spinal hook in accordance with the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
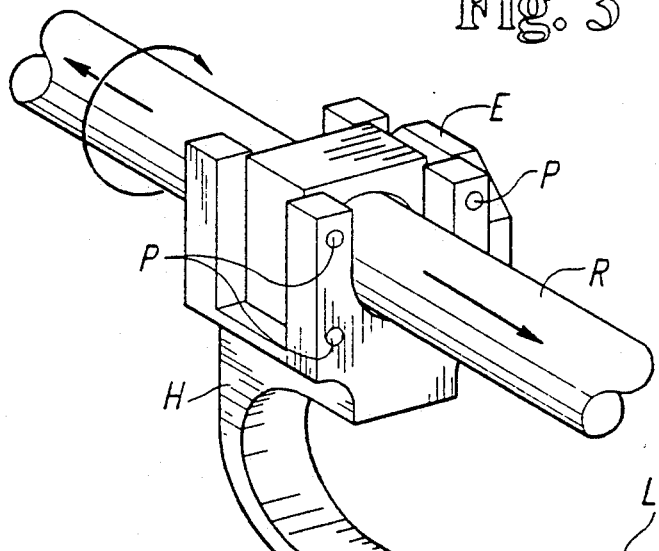
FIG. 1 shows a spinal hook engaged to a fixation rob by way of an eyebolt assembly as configured in accordance with the prior art configuration.
Figure 2:
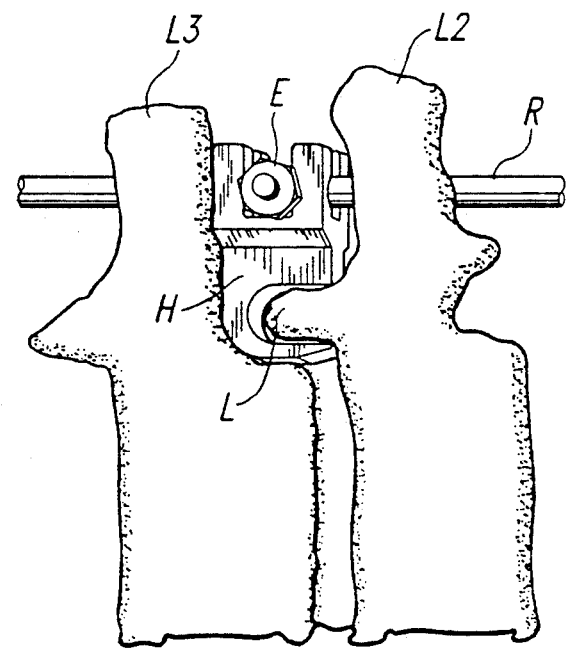
FIG. 2 is a side view showing the existing standard hook of FIG. 1 engaged about the lamina of the lumbar vertebra.

As discussed above, FIG. 1 illustrates a spinal hook H of a known standard design which is used as part of a spinal fixation system, such as the TSRH TM system of Danek Medical, Inc. The hook is fixed to a spinal rod R by way of an eyebolt assembly E. The hook H also includes a number of pinholes for engaging a conventional hook holder, such as the hook holder part number 808-036 of Danek Medical, Inc. The hook H depicted in FIG. 1 can be a hook such as the laminar hook part number 808-007 of Danek Medical, Inc. FIG. 2 shows the same hook H and spinal rod R engaged between the lumbar vertebra L2 and L3, specifically with the hook engaging the lamina L of the L2 vertebra. The spinal hook of the present invention to be described herein is intended as a substitute for this known hook H.

Figure 4:
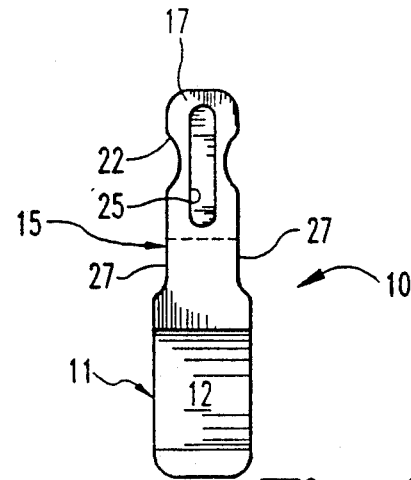
FIG. 4 is an end elevation of the spinal hook shown in FIG. 3.

One embodiment of the spinal hook of the present invention is depicted in FIGS. 3 and 4. In particular, the spinal hook 10 includes a shoe 11 having a bone-engaging surface 12. The bone-engaging surface 12 can be formed in a particular shape to engage a lamina of a vertebra, for instance. Integral with the shoe 11 of hook 10 is a top portion 15.

In accordance with the present invention, the top portion 15 includes a pair of posts 17 disposed apart from each other to form a slot 19 therebetween. The slot is wide enough to receive an eyebolt assembly, such as eyebolt assembly E shown in FIG. 1. A pair of coaxial grooves 22 are formed in each lateral surface 27 of both central posts 17. Each groove 22 is configured to receive a portion of a spinal rod such as rod R shown in FIG. 1. The rod grooves 22 are present on each lateral surface 27 of the central post 17 so that the hook 10 can be oriented on either side of a spinal rod.

In yet another feature of the invention, a slot 25 is formed in the outwardly facing end face 28 of each of the central posts 17. The slots 25 are preferably elongated and generally elliptical in shape and are cut into the post 17 to a sufficient depth for firm engagement by a hook-holding instrument, to be discussed herein.

Figure 5:
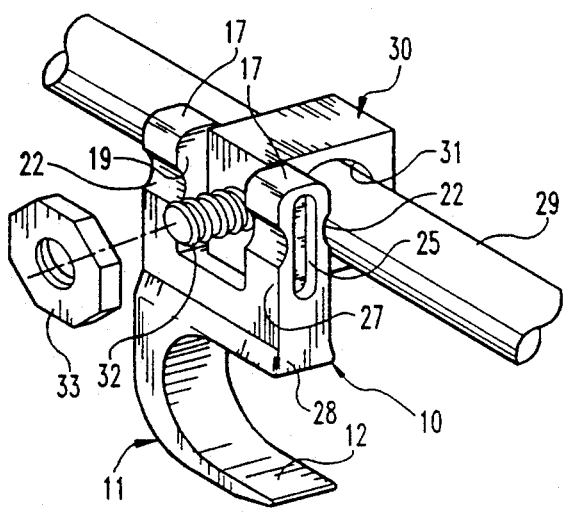
FIG. 5 shows the spinal hook of FIGS. 3 and 4 engaged on a spinal rob by way of an eyebolt assembly.

Referring now to FIG. 5, the manner of installing the hook 10 of the present invention is depicted. In particular, a spinal rod 29 is provided which extends through a rod bore 31 of an eyebolt assembly 30. The eyebolt assembly 30 projects through the slot 19 between the central posts 17 of the hook 10. The threaded post 32 of the eyebolt assembly also projects through the slot 19 for engagement with a nut 33. The nut 33 is then threaded onto the post 32 until it contacts a lateral surface 27 of the two central posts 17, thereby trapping the central posts between the rod 29 and the nut 33. The grooves 22 on the opposite lateral surfaces of the central posts 17 pinch a portion of the rod 29 to clamp the hook 10 to the rod. It should be apparent that the hook 10 could have been situated on the opposite side of the rod 29 with the rod engaged within the grooves 22 that are exposed in FIG. 5.

Figures 6, 7:
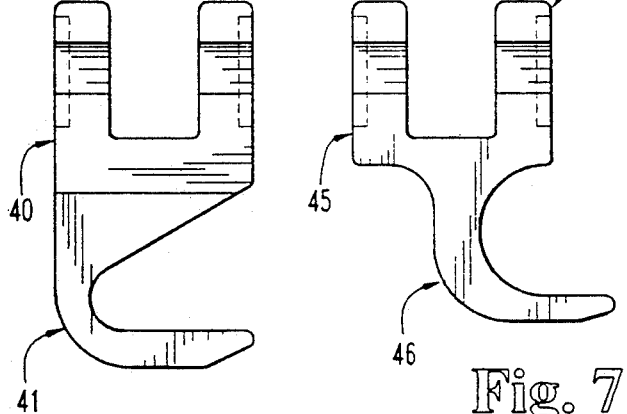
FIGS. 6-9 show alternative configurations of the spinal hook of the present invention for engaging different portions of the vertebra.
Figure 8:
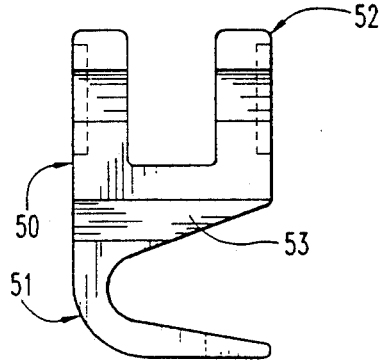
Figure 9:
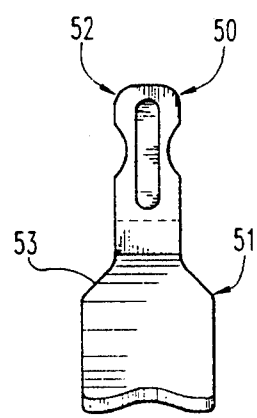

The hook of the present invention can be reconfigured for engaging different portions of the vertebral columns. For instance, as shown in FIG. 6, a hook 40 includes a shoe 41 configured for engaging the lamina of a thoracic vertebra. Similarly, the hook 45 of FIG. 7 includes a shoe 46 adapted to engage a transverse process, while hook 50 in FIG. 8 is a pedicle hook having a shoe 51 adapted to engage a pedicle. In each case, the top portion of each of these hooks, namely top 42 of the laminar thoracic hook, top 47 of the transverse process hook, and top 52 of the pedicle hook, are configured identically to the top portion 15 described above. While the central post hook of the present invention provides a narrower profile than the four-post hooks of the prior art, the bone-engaging surface can be enlarged for engaging a particular vertebral component, such as shown in FIGS. 8 and 9 for the pedicle hook 50. Specifically, the pedicle hook 50 includes a shoe 51 which is enlarged with respect to the shoes of the hook previously described. A transition section 53 is provided between the central post top 52 and the shoe 51.

Figure 10:
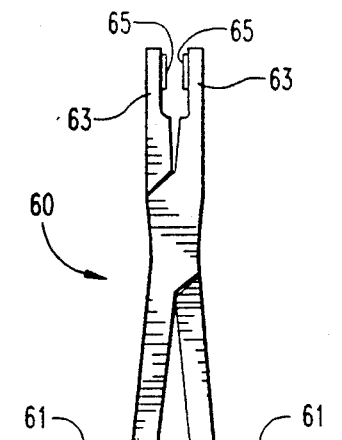
FIG. 10 is a top elevational view of hook-holding instrument adapted to engage the spinal hook of the present invention.

Referring now to FIG. 10, a hook holder 60 is shown which includes a pair of pivoted arms 61. Jaws 63 at the end of the arms 61 are configured for engaging the opposite end faces of a central post hook, such as hook 10 of the present invention. Specifically, the jaws include opposite inwardly facing tongues 65 which are configured to be received within the slots 25 in the end faces 28 of the central posts 17. The use of the tongue and slot arrangement is an improvement over the prior pin and pinhole arrangement for the hook-engaging instrument. The elongated areas of contact between the tongues 65 and the slots 25 provides a firmer engagement between the instrument 60 and the hook 10 that is not likely to be jarred loose or require excessive manipulation during implantation of the hook during connection to a fixation rod, such as rod 29. In addition, the tongue and slot configuration offers greater lateral and angular strength and restraint than does the prior art pinhole and pin designs.

In one specific embodiment for the hook 10 shown in FIGS. 3-5, the grooves 22 in the lateral faces of the central posts 17 have a diameter of 0.188 inches. It has been found that this groove diameter is sufficient to capture a larger rod, such as a rod having a diameter of 0.250 inches. In the specific embodiment, the slots 25 for engaging the hook-holder instrument have a length of 0.312 inches, a width of 0.067 inches, and a depth of 0.041 inches. The tongues 65 of the hook-holding instrument 60 must be similarly configured but having a length, width and height slightly smaller than the corresponding dimensions of the slot 25 to allow a sliding insertion. Again, in the specific embodiment, the width of each central post 17 is approximately 0.188 inches. Each of the edges of the central posts 17 is rounded to avoid trauma to soft tissue surrounding the vertebra to which the hook is engaged.

As is represented by FIGS. 6-9, the central post hook 10 of the present invention can be easily configured to engage a variety of vertebral portions. In fact, the range of available hook designs for the central post hook 10 of the present invention is the same as for the prior known four-post hook designs. Thus, the central post hook 10 of the present invention has the flexibility of the prior hook designs coupled with the additional flexibility of situating the hook on either side of the spinal rod depending on the requirements of the specific spinal anatomy. Moreover, the central post configuration offers a significantly reduced profile which reduces the risk of trauma to the patients, and which facilitates the implantation of the hooks 10, 40, 45 and 50 of the present invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

We claim:

1. A spinal hook for interengaging a fixation rod with the human spine, comprising:
   a shoe portion configured to engage a portion of a vertebra in the human spine; and
   a top portion integrally formed on said shoe portion, said top portion including only a plurality of posts projecting therefrom, each of said plurality of posts having mutually coplanar first lateral surfaces and each including a groove formed in said first lateral surface, each of said grooves being coaxial and adapted to engage the fixation rod,
   wherein each of said plurality of posts includes mutually coplanar second lateral surfaces opposite said first lateral surfaces, each of said second lateral surfaces including a second groove formed therein, each of said second grooves being coaxial and adapted to engage the fixation rod.

2. The spinal hook of claim 1 wherein said top portion is symmetrical about a plane extending parallel to and between said first and second lateral surfaces.

3. The spinal hook of claim 2 wherein said shoe portion is symmetric about said plane.

4. The spinal hook of claim 1 wherein a pair of said plurality of posts includes opposite outwardly facing end surfaces, each of said end surfaces having an elongated slot defined therein for engaging an insertion instrument.

5. The spinal hook of claim 1 wherein said plurality of posts includes only two posts.

6. A spinal hook for interengaging a fixation rod with the human spine, comprising:
   a shoe portion configured to engage a portion of a vertebra in the human spine; and
   a top portion integrally formed on said shoe portion, said top portion including only a plurality of posts projecting therefrom, each of said plurality of posts having mutually coplanar first lateral surfaces and each including a groove formed in said first lateral surface, each of said grooves being coaxial and adapted to engage the fixation rod,
   wherein said groove of each of said plurality of posts is defined at a groove radius, said groove radius being less than the effective radius of the fixation rod.

7. A spinal hook assembly for interengaging a fixation rod with the human spine comprising:
   an eyebolt assembly having a body with a bore for receiving the fixation rod, a threaded post projecting from the body and a nut for engaging the threaded post; and
   a spinal hook including;
      a shoe portion configured to engage a portion of a vertebra in the human spine; and
      a top portion integrally formed on said shoe portion, said top portion including only a plurality of posts projecting therefrom, said plurality of posts being displaced from each other to define a number of slots therebetween, at least one of said number of slots being sized to receive said body of said eyebolt assembly therethrough for fixing said spinal hook to the fixation rod,
      each of said plurality of posts having mutually coplanar first lateral surfaces and each including a groove formed in said first lateral surface, each of said grooves being coaxial and adapted to engage the fixation rod,
      each of said plurality of posts further having mutually coplanar second lateral surfaces opposite said first lateral surfaces, each of said second lateral surfaces including a second groove formed therein, each of said second grooves being coaxial and adapted to engage the fixation rod,
   whereby the spinal rod can be received in one of said first groove or second groove in the corresponding one of said first lateral surfaces or said second lateral surfaces, while said nut of said eyebolt assembly is threaded along said post extending through said one of said number of slots to clamp against the other of said first lateral surfaces or said second lateral surfaces.

* * * * *